United States Patent
Inokawa et al.

(10) Patent No.: US 10,207,253 B1
(45) Date of Patent: Feb. 19, 2019

(54) VANADIUM OXIDE CATALYST SUPPORTED ON CEO$_2$—ZRO$_2$ FOR FORMALDEHYDE PRODUCTION VIA PARTIAL OXIDATION OF METHANOL

(71) Applicant: King Abdulaziz University, Jeddah (SA)

(72) Inventors: Hitoshi Inokawa, Jeddah (SA); Sharif F. Zaman, Jeddah (SA); Muhammad A. Daous, Jeddah (SA); Abdulrahim Al-Zahrani, Jeddah (SA); Lachezar Petrov, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/729,989

(22) Filed: Oct. 11, 2017

(51) Int. Cl.
| | |
|---|---|
| *C07C 45/38* | (2006.01) |
| *B01J 23/00* | (2006.01) |
| *B01J 21/00* | (2006.01) |
| *B01J 35/00* | (2006.01) |
| *B01J 23/22* | (2006.01) |
| *B01J 35/10* | (2006.01) |
| *B01J 21/06* | (2006.01) |
| *B01J 23/10* | (2006.01) |

(52) U.S. Cl.
CPC ............ *B01J 23/22* (2013.01); *B01J 21/066* (2013.01); *B01J 23/10* (2013.01); *B01J 35/1009* (2013.01); *C07C 45/38* (2013.01)

(58) Field of Classification Search
CPC .. C07C 45/38; B01J 23/22; B01J 23/10; B01J 21/066; B01J 35/1009
See application file for complete search history.

(56) References Cited

U.S. PATENT DOCUMENTS

| | | |
|---|---|---|
| 5,907,066 A | 5/1999 | Wachs |
| 6,028,228 A | 2/2000 | Wachs |
| 6,497,855 B1 | 12/2002 | Wachs |
| 6,781,018 B2 | 8/2004 | Liu et al. |

FOREIGN PATENT DOCUMENTS

| | | |
|---|---|---|
| CN | 103933965 | 4/2016 |
| EP | 3 088 082 | 11/2016 |
| WO | 2014/083431 | 6/2014 |

OTHER PUBLICATIONS

P. Lakshmanan, "Design of Nanosized Ceria-Zirconia Mixed Oxides for Catalytic Applications," May 2006. 11 Pages.

Israel E. Wachs et al., "Methanol Oxidation Over Supported Vanadium Oxide Catalysts: New Fundamental Insights About Oxidation Reactions Over Metal Oxide Catalysts from Transient and Steady State Kinetics," 1997, vol. 109, pp. 305-314.

*Primary Examiner* — Sikarl A Witherspoon

(74) *Attorney, Agent, or Firm* — Oblon, McClelland, Maier & Neustadt, L.L.P.

(57) ABSTRACT

A vanadium oxide catalyst supported on a cerium oxide and zirconium oxide composite core is described. The catalyst comprises 0.1-3 wt % vanadium oxide relative to the total catalyst weight, and the catalyst is in the form of microparticles having diameters of 5-80 μm. A method using a wetness impregnation technique to produce the catalyst is described. The use of the catalyst in the partial oxidation of methanol to produce formaldehyde is specified, along with the catalyst's stability for reaction periods of 50 or more hours. A method of regenerating the catalyst for multiple reactions is also described.

19 Claims, 10 Drawing Sheets

VANADIUM OXIDE CATALYST SUPPORTED ON $CeO_2$—$ZrO_2$ FOR FORMALDEHYDE PRODUCTION VIA PARTIAL OXIDATION OF METHANOL

BACKGROUND OF THE INVENTION

Technical Field

The present invention relates to a vanadium oxide catalyst supported on cerium oxide and zirconium oxide, methods of synthesizing the catalyst, and methods of use in the production of formaldehyde.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Formaldehyde ($CH_2O$) is an important chemical used widely in industry. The primary uses of formaldehyde are in synthesis of urea-, phenol-, and melamine-formaldehyde-based resins, polymers, and chemicals (e.g. 1,4-butanediol, methylene diisocyanate and amino polycarboxylic acids). Other industrial uses of formaldehyde include its role as an embalming agent and gasoline stabilizer. Global demand of formaldehyde in 2015 was 46 million tons and is expected to grow to 58 million tons by the end of 2020. See Andersson, L-O., "Formaldehyde expected to grow beyond GDP globally," *Informally Speaking*, J M Formox, Autumn 2015, 8, incorporated herein by reference in its entirety.

Formaldehyde may be produced by the catalytic partial oxidation of methanol. Initially copper oxide was used as the catalyst, and later, silver and Mo—Fe oxide catalysts were introduced.

Vanadium oxide has also been studied as a catalyst for formaldehyde production via the partial oxidation of methanol. The catalytic process shows high selectivity towards formaldehyde in the 150-250° C. temperature range. Because of this low temperature regime, the methanol conversion is low. Methanol conversion may be increased at higher temperatures, such as higher than 250° C., but here the formaldehyde selectivity is significantly decreased. In addition, a number of by products, such as carbon monoxide and carbon dioxide, are produced.

As mentioned previously, metallic silver catalysts or composite-supported silver and Mo—Fe oxide catalysts have been introduced for the partial oxidation of methanol, and these catalysts are currently used in industry.

The partial oxidation of methanol on a metallic silver catalyst is carried out at temperatures between 600° C. and 700° C., with a 1:1 volume ratio of air to methanol entering the reactor. The reaction proceeds in an external diffusion regime, at short contact time less than 0.01 s, with a degree of conversion close to thermodynamic equilibrium. However, silver catalysts are sensitive to catalyst poisons. During the reaction, coke forms on the surface of the catalyst, which substantially changes the catalyst structure. Gases at the reactor exit are rich in hydrogen, and dehydrogenation takes place at the same time as the partial oxidation.

The partial oxidation of methanol using silver catalysts suffers from several disadvantages, as outlined below:

1) The reaction temperature is very high, above 650° C.;
2) The process is carried out in external diffusion regime;
3) The silver catalyst is very sensitive to catalyst poisons, and thus requires a very clean oxidizing agent;
4) During the catalytic process coke is deposited on the catalyst surface;
5) Because of very high reaction temperature, metal silver particles are re-crystalyzed and finally sintered;
6) The prices of silver salts are growing steadily, which make the silver catalysts relatively expensive;
7) During the partial oxidation of methanol, a large amount of hydrogen is evolved.

The partial oxidation of methanol on a Mo—Fe oxide catalyst is carried out at temperatures between 350° C. and 400° C. and with a 98-99% degree of conversion. The reaction mixture contains a mixture of air and 6-9 vol % methanol. The active catalyst contains $Fe_2(MoO_4)_3$ and free $MoO_3$. The system can be promoted by oxides of V, Cr, and/or Co, which stabilize the structure of $Fe_2(MoO_4)_3$. At higher methanol concentrations the catalyst is coked and deactivated. The reaction proceeds via the van Krevelen redox mechanism.

The partial oxidation of methanol using Mo—Fe oxide catalysts suffers from several disadvantages, as outlined below:

1) The catalyst is composed of pelletized bulk mixed oxides. Since the working temperature is relatively high, 350-400° C., and degree of conversion is very high, the reaction likely proceeds in the internal diffusion regime;
2) The Mo—Fe oxide catalyst is very sensitive to overheating, which may cause catalyst sintering;
3) With increasing methanol concentrations, the catalyst may become partially reduced and deactivated.

Therefore, the development of a highly effective yet inexpensive catalyst system for the oxidation of methanol to formaldehyde is of great value.

Roozeboom et al. reported a $V_2O_5$ catalyst supported on $CeO_2$, $ZrO_2$, $TiO_2$, and $Al_2O_3$. $V_2O_5$ on $CeO_2$ showed high formaldehyde selectivity ($\approx$100%) at a temperature range of 150° C. to 180° C. See Roozeboom, F. et al., *Journal of Catalysis*, 68 (1981) 464-472, incorporated herein by reference in its entirety. The methanol conversion, however, was less than 10%. At temperatures higher than 180° C., methanol conversion was increased, but formaldehyde selectivity was significantly decreased as a result of dimethyl-ether (DME) generation. $V_2O_5$ catalysts supported on $TiO_2$ and $ZrO_2$ also showed high selectivity to formaldehyde at low temperatures (between 150° C. and 200° C.), but also suffered from low conversion of methanol due to the formation of dimethyl-ether. Israel E. Wachs reported a $VO_x$ catalyst supported on $Al_2O_3$, $ZO_2$, $TiO_2$, $Nb_2O_5$, and $SiO_2$. See Wachs, I. E., *Applied Catalysis A: General*, 391 (2011) 36-42, incorporated herein by reference in its entirety. The catalysts showed high selectivity for formaldehyde (between 50 and 100%) at 230° C. The observed methanol conversion, however, was about 10%.

Although vanadium oxide has demonstrated some attractive properties as a catalyst for the selective partial oxidation of methanol to formaldehyde, $V_2O_5$ based catalysts have shown low methanol conversion and/or low selectivity to formaldehyde. A summary of reported catalysts for the partial oxidation of methanol to formaldehyde and their catalytic activity are given in Table 1.

TABLE 1

List of reported catalysts for the partial oxidation of methanol to formaldehyde.

| Catalyst | T (° C.) | $O_2$/MeOH ratio | Selectivity to $CH_2O$ (%) | Conversion (%) | Reference* |
|---|---|---|---|---|---|
| $VO_x$ on $Al_2O_3$, $ZrO_2$, $TiO_2$, $Nb_2O_5$, $SiO_2$ | 230 | 2 | 50-100 | 10% | Wachs, et al. |
| $V_2O_5$ on $SiO_2$, $ZrO_2$, $TiO_2$, $Nb_2O_5$, $Al_2O_3$ | 230 | 2 | >90% | <20% | Deo, et al. |
| $V_2O_5$, on $Al_2O_3$, $TiO_2$, $CeO_2$, $ZrO_2$ | 180 | 6 | 100 | 10 | Roozeboom, et al. |
| Industrial Mo based catalyst | 275 | 4 | 76 | 83.3 | Dias, et al. |

*See Wachs, I.E., *Applied Catalysis A: General*, 391 (2011) 36-42; Deo, G. and I.E. Wachs, *Journal of Catalysis*, 146 (1994) 323-334; Roozeboom, F. et al., *Journal of Catalysis*, 68 (1981) 464-472; and Dias, A.P.S. et al., *Journal of Molecular Catalysis A: Chemical*, 397 (2015) 93-98, each incorporated herein by reference in its entirety.

In view of the foregoing, one objective of the present invention is to provide a composition of highly effective and inexpensive vanadium oxide catalyst for the partial oxidation of methanol to formaldehyde, specifically a vanadium oxide catalyst supported on a $CeO_2$—$ZrO_2$ mechanically mixed carrier. The present invention also provides a method of making this catalyst, and a method of using the catalyst in the partial oxidation of methanol to produce formaldehyde.

BRIEF SUMMARY OF THE INVENTION

According to a first aspect, the present disclosure relates to a vanadium oxide catalyst, comprising a $CeO_2$ and $ZrO_2$ composite core decorated with vanadium oxide nanoparticles. The vanadium oxide nanoparticles have diameters of 1-10 nm. The vanadium oxide catalyst has a diameter of 5-80 μm and 0.1 to 3 wt % vanadium relative to a total weight of the vanadium oxide catalyst.

In one embodiment, the vanadium oxide catalyst has a surface area of 5-10 $m^2 \cdot g^{-1}$.

In one embodiment, the vanadium oxide catalyst has a Ce to Zr mass ratio of 2.0:1.0 to 3.5:1.0.

In one embodiment, the vanadium oxide is $V_2O_5$.

According to a second aspect, the present disclosure relates to a method for producing the vanadium oxide catalyst of the first aspect. This method involves sonicating $CeO_2$ powder and $ZrO_2$ powder in a liquid suspension to form a mixed oxide; mixing the mixed oxide with a vanadium precursor to form an aqueous suspension; drying the aqueous suspension to produce a dried catalyst precursor; heating the dried catalyst precursor at 450-700° C. for 2-8 hours to produce a calcined powder; and pelletizing and grinding the calcined powder to produce the vanadium oxide catalyst.

In one embodiment of the method, the aqueous suspension has a vanadium concentration of 0.05-1.0 M.

In one embodiment of the method, the vanadium precursor is one selected from the group consisting of ammonium metavanadate, potassium metavanadate, sodium metavanadate, bismuth vanadate, vanadium oxytrichloride, and vanadium pentafluoride.

In one embodiment of the method, the vanadium precursor is ammonium metavanadate.

According to a third aspect, the present disclosure relates to a method of partially oxidizing methanol into formaldehyde. This method involves feeding a gas stream comprising $O_2$ and methanol to a catalyst bed comprising the vanadium oxide catalyst of claim 1 at a temperature of 275-380° C. to produce formaldehyde and at least one side product selected from the group consisting of hydrogen gas, carbon monoxide, carbon dioxide, water, and dimethyl ether.

In one embodiment, the gas stream has an $O_2$ to methanol molar ratio of 0.5:1.0 to 0.8:1.0.

In one embodiment, the gas stream is fed to the catalyst bed at a gas hourly flow rate per g of the vanadium oxide catalyst of 25,000-35,000 $cm^3 \cdot h^{-1} \cdot g^{-1}$.

In one embodiment, a mole percentage of formaldehyde produced with respect to moles methanol consumed is at least 90%.

In a further embodiment, where a mole percentage of formaldehyde produced with respect to moles methanol consumed is at least 90%, the gas stream has an $O_2$ to methanol molar ratio of 0.55:1.0 to 0.65:1.0.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein. "compound" is intended to refer to a chemical entity, whether as a solid, liquid, or gas, and whether in a crude mixture or isolated and purified.

As used herein, "the catalyst" refers to the vanadium oxide catalyst of the first aspect of the disclosure, unless otherwise indicated.

As defined here, "composite" refers to a combination of two or more distinct constituent compounds into one solid object, such as a particle, where the individual constituent compounds, on an atomic level, remain separate and distinct within the finished structure.

Figure 2:
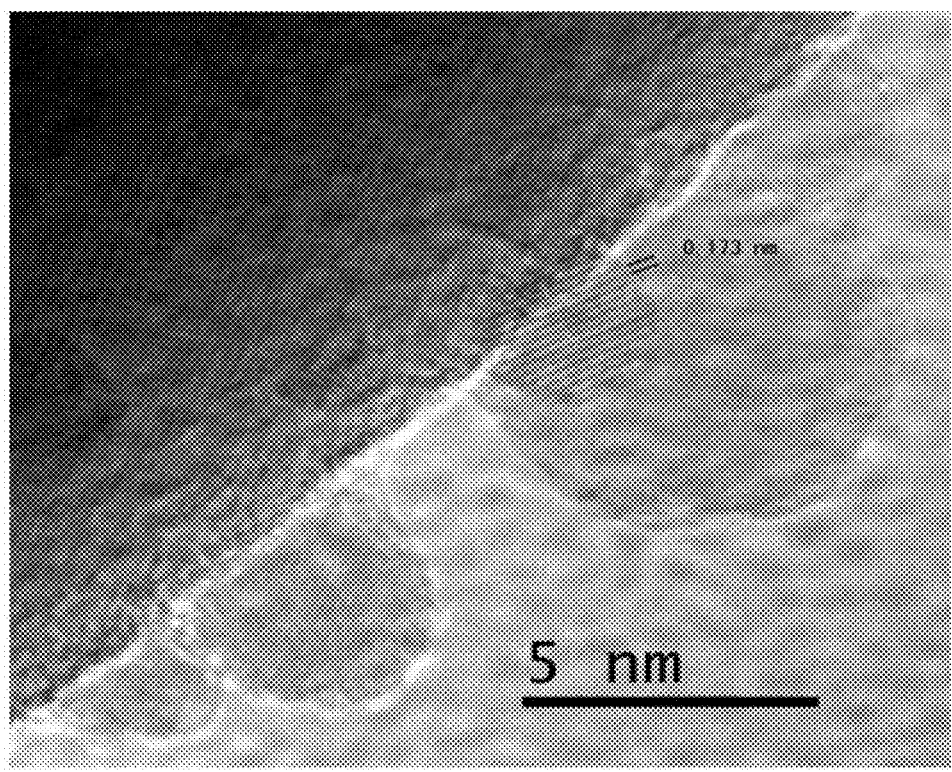
FIG. 2 is a TEM image of a vanadium oxide catalyst with 1 wt % vanadium.

According to a first aspect, the present disclosure relates to a vanadium oxide catalyst (i.e. "the catalyst"), comprising a $CeO_2$ and $ZrO_2$ composite core decorated with vanadium oxide nanoparticles. The vanadium oxide catalyst has a diameter of 5-80 μm, preferably 10-75 μm, more preferably 30-70 μm. The catalyst has elemental vanadium (V) present at 0.1-3 wt %, preferably 0.5-2.5 wt %, more preferably 0.9-2 wt % relative to the total weight of the catalyst. The vanadium oxide nanoparticles have diameters of 1-10 nm, preferably 1-8 nm, more preferably 2-5 nm. In one embodiment, the catalyst comprises 6-80 wt %, preferably 63-75 wt %, more preferably 65-70 wt % $CeO_2$ relative to a total weight of the catalyst; and 20-32 wt %, preferably 22-31 wt %, more preferably 25-30 wt % $ZrO_2$ relative to a total weight of the catalyst. The catalyst may have a $CeO_2$ to V mass ratio of 10.0:1.0-60.0:1.0, preferably 15.5:1.0-55.0:1.0, more preferably 17.0:1.0-52.0:1.0, even more preferably 40.0:1.0-50.0:1.0. The catalyst may have a $ZrO_2$ to V mass ratio of 2.0:1.0-30.0:1.0, preferably 3.5:1.0-25.0:1.0, more preferably 6.0:1.0-24.0:1.0, even more preferably 15.0:1.0-23.0:1.0. FIG. 2 shows a TEM image of the vanadium oxide catalyst in one embodiment. The catalyst may have physical or chemical properties that are different than individual components each of $CeO_2$, $ZrO_2$, and vanadium oxide.

In one embodiment, the $CeO_2$ and $ZrO_2$ composite core may be a nanocomposite, where one of the constituent materials or phases has one, two, or three dimensions of less than 100 nanometers, or structures having nanoscale repeat distances between the different phases that make up the material. In another embodiment, the catalyst may have domains of constituent materials or phases that are larger than a nanocomposite, for example, where the dimension or structure of a constituent material or phase is about 100 nm-40 μm, preferably 400 nm-10 μm, or 500 nm-1 μm.

The vanadium oxide nanoparticles may cover 10-90%, preferably 20-80%, more preferably 20-50% of the total surface area of the composite core. In one alternative embodiment, vanadium oxide may cover 98-100% of the total surface area of the composite core, as either vanadium oxide nanoparticles, or as a vanadium oxide layer having a thickness of 1-10 nm, preferably 1-8 nm, more preferably 2-5 nm. In another alternative embodiment, the $CeO_2$ and $ZrO_2$ composite core may be impregnated with vanadium oxide nanoparticles, for instance, forming a nanocomposite of $CeO_2$, $ZrO_2$, and vanadium oxide where some nanodomains of vanadium oxide may be completely surrounded by $CeO_2$ and/or $ZrO_2$.

In one alternative embodiment, the catalyst may be in the form of agglomerates. As used herein, the term "agglomerates" refers to a clustered particulate composition comprising primary particles, the primary particles being aggregated together in such a way so as to form clusters thereof, at least 50 volume percent of the clusters having a mean diameter that is at least 2 times the mean diameter of the primary particles, and preferably at least 90 volume percent of the clusters having a mean diameter that is at least 5 times the mean diameter of the primary particles. The primary particles may be $CeO_2$ and $ZrO_2$ microparticles having a mean diameter of 1-40 μm, preferably 1.5-30 μm, more preferably 2-20 μm. The vanadium oxide may be present as nanoparticles with diameters as those mentioned previously or as particles having a mean diameter of 20 nm-5 μm, preferably 30 nm-1 μm, more preferably 40 nm-400 nm. The vanadium oxide may form an amorphous phase, a crystalline phase, or both. These primary particles of $CeO_2$ and $ZrO_2$ and may cluster together with vanadium oxide as agglomerates having diameters of 5-80 μm, preferably 10-75 μm, more preferably 30-70 μm. In one embodiment, the agglomerates may have diameters greater than 70 μm.

In one embodiment, the catalyst may comprise vanadium oxide at a greater amount, resulting in a vanadium weight percentage of 3-10 wt %, or 10-20 wt %, per total catalyst weight. In one embodiment, the catalyst may comprise additional chemical species. These compounds may be those with catalytic properties such as titanium oxide, molybdenum oxide, a zeolite, copper, zinc oxide, silver, platinum, nickel, palladium, or polyaniline, and may be present in an amount of 0.1-14.5 wt %, preferably 1-10 wt %, more preferably 2-6 wt % relative to the total weight of the catalyst. Alternatively, an additional component/compound may function as a support, such as silica, alumina, potassium oxide, or magnesium chloride, and may be present in an amount of 0.1-14.5 wt %, preferably 1-10 wt %, more preferably 2-6 wt % relative to the total weight of the catalyst, though in alternative embodiments, may be present at a higher weight percent.

In one embodiment, the vanadium oxide catalyst has a surface area of 5-10 $m^2 \cdot g^{-1}$, preferably 6-9 $m^2 \cdot g^{-1}$, more preferably 7.5-8.5 $m^2 \cdot g^{-1}$. The surface area may be determined by mercury intrusion porosimetry, Brunauer-Emmett-Teller (BET) analysis of $N_2$ adsorption isotherms, or some other technique. Preferably the surface area is determined by BET analysis of $N_2$ adsorption isotherms. In one embodiment, the catalyst may be a porous material, having pore sizes of 1-100 nm, preferably 2-40 nm, more preferably 3-20 nm.

In one embodiment, the vanadium oxide catalyst has a Ce to Zr mass ratio of 2.0:1.0 to 3.5:1.0, preferably 2.2:1.0 to 3.4:1.0, more preferably 2.8:1.0 to 3.3:1.0.

The vanadium oxide may comprise VO (vanadium(II) oxide), $V_2O_3$ (vanadium(III) oxide), $VO_2$ (vanadium(IV) oxide), and/or $V_2O_5$ (vanadium(V) oxide, or vanadia). The vanadium oxide may also comprise distinct phases such as $V_3O_7$, $V_4O_9$, $V_6O_{13}$, and Magnéli phases such as $V_4O_7$, $V_5O_9$, $V_6O_{11}$, $V_7O_{13}$, and $V_8O_{15}$. In one embodiment, the vanadium oxide comprises a majority of $V_2O_5$, for example, 70-100 mol %, preferably 80-100 mol %, more preferably 90-100 mol % of the total vanadium in the catalyst is present as $V_2O_5$. In one preferred embodiment, all of the vanadium oxide in the catalyst is $V_2O_5$. In an alternative embodiment, the vanadium may be present at greater than 3 wt % of the total catalyst weight, for example, 3-15 wt %, or 10-20 wt %.

According to a second aspect, the present disclosure relates to a method for producing the vanadium oxide catalyst of the first aspect. This method involves sonicating $CeO_2$ powder and $ZrO_2$ powder in a liquid suspension to form a mixed oxide; mixing the mixed oxide with a vanadium precursor to form an aqueous suspension; drying the aqueous suspension to produce a dried catalyst precursor; heating the dried catalyst precursor at 450-700° C. for 2-8 hours to produce a calcined powder; and pelletizing and grinding the calcined powder to produce the vanadium oxide catalyst.

$CeO_2$ powder and $ZrO_2$ powder may be mixed with water to form the liquid suspension. The $CeO_2$ and $ZrO_2$ powders may comprise particles of $CeO_2$ and $ZrO_2$ having diameters of 20 nm-100 μm, preferably of 50 nm-10 μm, more preferably 100 nm-5 μm. In one embodiment, the $CeO_2$ and $ZrO_2$ powders may be premixed before mixing with water. In an alternative embodiment, the $CeO_2$ and $ZrO_2$ powders may comprise one or more particles containing both $CeO_2$ and $ZrO_2$, at a Ce:Zr molar ratio of 1:10-10:1, preferably 1:5-5:1, more preferably 1:4-4:1. In another embodiment, particles of the $CeO_2$ and $ZrO_2$ powders may have surface areas of 10-200 m²/g, preferably 20-150 m²/g, more preferably 50-120 m²/g.

The oxide powders ($CeO_2$ powder and $ZrO_2$ powder) may be present in the liquid suspension at 20-60 wt %, 30-50 wt %, more preferably 42-46 wt % of the total liquid suspension weight. The oxide powders may have a $CeO_2$ to $ZrO_2$ mass ratio of 2:1-4:1, preferably 2.5:1-3.5:1, more preferably 2.8:1-3.2:1. In one embodiment, 28-32 g $CeO_2$ powder and 9-11 g $ZrO_2$ powder is mixed with every 48-52 mL of water to form the liquid suspension. The liquid suspension may then be sonicated for 0.25-3 h, preferably 0.5-2 h, more preferably 0.75-1.25 h in a bath sonicator. Alternatively, a probe tip sonicator may be used instead of a bath sonicator. The sonication produces a mixed oxide in water, which mixed oxide may then be removed from suspension and dried. The mixed oxide may be separated by filtering, centrifuging, and/or evaporating the liquid suspension, and may then be dried in an oven at 80-150° C., preferably 100-140° C., more preferably 110-130° C., for 3-24 h, preferably 10-20 h, more preferably 12-18 h. Alternatively, the mixed oxide may be dried in a desiccator, with or without a vacuum, or under a flow of inert gas, such as argon or nitrogen. However, in one embodiment, the mixed oxide may not be dried or removed from the liquid suspension.

The mixed oxide is mixed with a vanadium precursor to form an aqueous suspension. In one embodiment, the aqueous suspension has an elemental vanadium concentration of 0.05-1.0 M, preferably 0.05-0.5 M, more preferably 0.08-0.2 M, resulting from the presence of the vanadium precursor. Alternatively, the vanadium precursor may be added to a certain weight percentage of the aqueous suspension, for example, 0.01-10 wt of the total aqueous suspension, preferably 0.1-5 wt %, more preferably 0.5-2 wt %.

In one embodiment, the vanadium precursor is at least one selected from the group consisting of ammonium metavanadate, potassium metavanadate, sodium metavanadate, bismuth vanadate, vanadium oxytrichloride, and vanadium pentafluoride. In alternative embodiments, the vanadium precursor may be vanadium metal, sodium decavanadate, sodium orthovanadate, yttrium orthovanadate, vanadium carbide, vanadium hexacarbonyl, vanadium nitride, vanadium phosphate, vanadium tetrachloride, vanadium tetrafluoride, vanadium-gallium, vanadium(II) bromide, vanadium(II) chloride, vanadium(III) bromide, vanadium(III) chloride, vanadium(II) fluoride, vanadium(III) iodide, vanadium(III) sulfate, vanadium(V) oxytrifluoride, vanadium (III) acetylacetonate, vanadyl acetylacetonate, vanadyl nitrate, vanadyl perchlorate, or vanadyl sulfate. In an alternative embodiment, vanadium oxide, in any of the formulas as mentioned previously for the catalyst, may be used in place of the vanadium precursor.

In a preferred embodiment, the vanadium precursor is ammonium metavanadate ($NH_4VO_3$). In this embodiment, the ammonium metavanadate may be mixed or dissolved to form a vanadium precursor solution comprising 0.5-2 wt % vanadium or vanadate ion. Alternatively, 10-13 g, preferably 11-12 g ammonium metavanadate may be dissolved per every L of water in this vanadium precursor solution. To increase the solubility of the ammonium metavanadate, this vanadium precursor solution may be heated to 35-80° C., preferably 50-70° C., while stirring or agitating.

In one embodiment, the mixed oxide is mixed into the vanadium precursor solution to result in an aqueous suspension having a combined $CeO_2$ and $ZrO_2$ weight percentage of 25-40 wt %, preferably 30-35 wt % of the aqueous suspension weight. In a preferred embodiment, the mixed oxide is dried before being mixed into the vanadium precursor solution; however, the liquid suspension containing the mixed oxide may be mixed without drying. In one embodiment, the aqueous suspension may be sonicated or heated to increase the vanadium salt dispersion or dissolution.

The aqueous suspension may then be dried to produce a dried catalyst precursor. The drying may be done by spray-drying, freeze drying, evaporation at ambient conditions, evaporation in a desiccator, evaporation in an oven, evaporation under a stream of inert gas such as $N_2$ or Ar, and/or evaporation under a vacuum. In one embodiment, the aqueous suspension is evaporated in a rotary vacuum evaporator operating at a temperature of 32-55° C., preferably 35-50° C., more preferably 38-45° C., and at an absolute pressure of 10-100 mbar, preferably 20-80 mbar, more preferably 30-70 mbar. The aqueous suspension may optionally be filtered before the drying, in order to quickly separate the Ce, Zr, and vanadium solid compounds from the aqueous suspension and reduce the drying time.

The dried catalyst precursor may be further dried in an oven at 70-150° C., preferably 80-130° C., more preferably 100-120° C., for 1-5 h, preferably 2-4 h. The catalyst precursor may then be calcined by heating at 450-700° C., preferably 450-600° C., more preferably 475-525° C. in static air for 2-8 h, preferably 2-6 h, more preferably 2.5-3.5 h. Between the oven drying and the calcination, the catalyst precursor may be allowed to cool below 70-150° C., or may be allowed to cool to room temperature. Alternatively, the dried catalyst precursor may not be cooled between the oven drying and the calcination. For example, the dried catalyst precursor may be heated at 70-150° C. in an oven, and then the temperature of the oven may be increased to 450-700° C. to calcine the dried catalyst precursor. In another embodiment, the dried catalyst precursor may be removed from the drying oven and immediately placed in a second oven preheated to 450-700° C. for the calcination. In one embodiment of the method, after the oven drying, the dried catalyst precursor is allowed to cool to a temperature of 20-35° C., preferably 22-32° C., more preferably 20-30° C., preferably by sitting at room temperature, and is then placed in an oven having an equivalent temperature, or a temperature of 20-35° C. The oven temperature may then be increased at a rate of 3-6° C./min, preferably 4-6° C./min, more preferably about 5° C./min to reach a previously mentioned calcination temperature.

Following the calcination, the oven may be turned off and allowed to cool to room temperature, or the calcined catalyst precursor may be removed and allowed to cool to room temperature.

In one embodiment, the calcined powder is pelletized and ground to produce the catalyst. The pelletizing may produce pellets which are defined here as self-sustaining solids that retain at least 25% of the surface area per mass of the starting calcined powder. The pelletizing may be done with a rotary drum pelletizer, a pan pelletizer, or a pellet press, and the calcined powder may be subjected to pressures of 50-6,000 psi, preferably 100-5,000 psi, more preferably 500-3,000 psi. The pellets may have a longest diameter of 3-20 mm, preferably 4-15 mm, and a shortest diameter of 1-10 mm, preferably 2-8 mm. Preferably the pellets are formed in a prismatic shape, such as a cylinder or a rectangular prism, though in other embodiments, the pellets may be formed into spherical or hemispherical shapes.

In another embodiment, the calcined powder may be pressed together into one single solid, such as a disc or cylinder, rather than individual pellets. The grinding may be with a mortar and pestle, a burr mill, a blade grinder, sandpaper, a ball mill, a disc mill, a jet mill, a conical mill, a hammer mill, or some other milling or grinding machine.

Preferably, the pelletizing and grinding is performed in order to increase the population of particles having a particle size between 5-80 μm, preferably 10-80 μm, more preferably 30-80 μm, as mentioned previously for the catalyst. However, the pelletizing and grinding may be carried out to produce particles having some other size range, shape, or to change the average surface area of the powder. In one embodiment, the calcined powder may be screened through a mesh or sieve to select for catalyst particles having a certain size, without the step of pelletizing and grinding. In another embodiment, the calcined powder may have an average particle size that is larger than desired, and thus may be ground and screened for a particle size range without a step of pelletizing. In another embodiment, catalyst particles larger or smaller than a certain particle size range may be repeatedly pelletized and/or ground. The screening or sieving of the particles may include a vibrating screen, a gyrating screen, a trommel screen, or some other mechanical separation device.

In an alternative embodiment, prior to the pelletizing, a binding agent or binder may be added to the catalyst powder. This binder may inhibit the interaction of contaminants in the reactor with the catalyst. The binder may form an aggregate with the catalyst, enhance the catalyst's temperature and/or mechanical stability, or provide a specified structure for the catalyst to take a shape. The binder may be a cellulosic polymer, a resin, calcium phosphate, or a combination thereof, and may have weight percent of 1-80 wt %, preferably 5-50 wt %, more preferably 10-30 wt % within the catalyst. For example, an organic thermoplastic resin binder may be employed to form a porous matrix for the catalyst in a small particle or pellet form. A cellulosic polymer may be used to provide a disordered porous fiber on which the catalyst may be distributed. With certain binders in use, pellets may be formed with less than 50 psi pressure applied, or with almost no pressure applied. In an alternative embodiment, $CeO_2$ powder, $ZrO_2$ powder, and a vanadium precursor may be mixed together and pelletized, without the step of dissolving in water, drying, or calcining.

According to a third aspect, the present disclosure relates to a method of partially oxidizing methanol into formaldehyde. The complete oxidation of methanol with $O_2$ leads to carbon dioxide and water as products while the partial oxidation of methanol with $O_2$ leads to products of formaldehyde and water. This method involves feeding a gas stream comprising $O_2$ and methanol to a catalyst bed comprising the vanadium oxide catalyst of the first aspect to produce formaldehyde and at least one side product selected from the group consisting of hydrogen gas, carbon monoxide, carbon dioxide, water, and dimethyl ether. In practice, both partial and complete oxidation reactions of methanol may occur, along with other side reactions. From these side reactions, other products such as formic acid, methane, and methyl formate may be produced. The type of methanol reaction taking place (partial oxidation, complete oxidation, or some side reaction) may not be related to the amount of methanol converted.

In one embodiment, the gas stream is fed to the catalyst bed in a fixed bed reactor at a flow rate of 40-60 cm$^3$/min, preferably 42-58 cm$^3$/min, more preferably 45-55 cm$^3$/min per 0.1 g of the vanadium oxide catalyst. The fixed bed reactor may be maintained at a temperature of 275-380° C., preferably 300-375, more preferably 320-375° C. In one embodiment, the gas stream has an $O_2$ to methanol molar ratio of 0.5:1.0-0.8:1.0, preferably 0.5:1.0-0.7:1.0, more preferably 0.55:1.0-0.65:1.0. In one embodiment, the gas stream further comprises 60-85 vol %, preferably 62-82 vol %, more preferably 65-80 vol % of an inert carrier gas relative to the total volume of the gas stream. Preferably the inert gas is helium, argon, or nitrogen, though in other embodiments the gas may be any gas that is not reacted or converted, and preferably does not affect the catalytic process beyond changing flow rates or concentrations. In an alternative embodiment, a carrier gas may be used that is the same species as one of the products of the oxidative reduction of methanol, for example, $CO_2$. In another alternative embodiment, the gas stream fed to the fixed bed reactor consists of only $O_2$ and methanol without a carrier gas. Before entering the fixed bed reactor, the gas stream may be heated to 100-200° C., preferably 120-180° C., more preferably 140-160° C.

Prior to the reaction, the fixed bed reactor may be heated to a reaction temperature of 275-425° C., preferably 300-400° C., more preferably 320-380° C. The fixed bed reactor may reach this reaction temperature by increasing its internal temperature at a rate of 2-8° C./min, preferably 3-7° C./min, more preferably 4-6° C./min.

In one embodiment, the gas stream is fed to the fixed bed reactor at a gas hourly flow rate per g catalyst of 25,000-35,000 cm$^3 \cdot$h$^{-1} \cdot$g$^{-1}$, preferably 27,000-33,000 cm$^3 \cdot$h$^{-1} \cdot$g$^{-1}$, more preferably 28,000-32,000 cm$^3 \cdot$h$^{-1} \cdot$g$^{-1}$. In one embodiment, the absolute pressure of the gas stream in the fixed bed reactor may be 0.5-1.5 atm, preferably 0.7-1.4 atm, more preferably 0.8-1.2 atm.

Contacting the catalyst with the gas stream at the reaction temperature may result in a conversion of the methanol and O$_2$ reactants into gas phase products such as formaldehyde, CO, CO$_2$, H$_2$, H$_2$O, and/or dimethyl either. Other side products such as methane, formic acid, and methyl formate may be produced. The flow of the gas stream allows the displacement of the gas phase products and unconverted methanol and O$_2$. These species can then be separated by one or more molecular sieve, adsorbent, or trapping agent and analyzed to determine concentrations. The molecular sieve, adsorbent, or trapping agent may be carbon based adsorbents, such as activated carbon, charcoal, or the Carbopak® series, porous polymers, such as the Chromosorb® series, the Porapak® series, the Tenax® series, the HayeSep® series, the XAD® series, clays, diatomaceous earth, magnesium silicates, such as Florisil®, ashes, micronized silicon dioxide, christobalite, hydrated sodium calcium aluminosilicates, chitosan, granulas, anionic ion exchange resins, cationic ion exchange resins, modified ion exchange resins, zeolites, perlite, bentonite, C4-30 aliphatic hydrocarbons, C4-30 unsaturated hydrocarbons, gas chromatography stationary phases, liquid chromatography stationary phases, polyethylene glycol with a melting point in the range from 30 to 100° C., preferably 40 to 50° C., silica gel, aluminum oxide, cellulose, granulates, high boiling point liquids such as polysiloxanes, phenyl substituted stationary phases, bases, acids, and diethylene glycol succinate derivatives. The powder forms of molecular sieves may be of type 3A, 4A, 5A, and 13X. Following separation, a GCMS, such as an HP G1540A, or a mass spectrometer may be used to determine concentrations. Alternatively, a GCMS may be used without a molecular sieve or without prior separation of the products. In an alternative embodiment, the exit gas stream may be condensed to form a liquid mixture, which is then analyzed. In one embodiment, before the exit gas stream is analyzed, the reaction may be allowed to run for 1-6 h, preferably 2-4 h, more preferably 2.5-3.5 h at specific reaction conditions so that the reaction products achieve steady state concentrations.

The success of the reaction may be determined by the percent conversion of the reactants and the percent selectivity of the gas phase products. Based on these values, a person having ordinary skill in the art may be able to determine preferable reaction parameters.

The percentage conversion of a reactant is a mol % of the reactant converted into one or more products, based on the total reactant fed to the reactor. This may be determined by subtracting the unreacted amount of reactant (such as CH$_3$OH$_{out}$) from the total amount of reactant fed (such as CH$_3$OH$_{in}$), dividing by the total amount of reactant fed, and converting to a percentage. The percentage conversions for methanol (CH$_3$OH) and O$_2$ are then:

$$\text{CH}_3\text{OH conversion (\%)} = \frac{\text{mol CH}_3\text{OH}_{in} - \text{mol CH}_3\text{OH}_{out}}{\text{mol CH}_3\text{OH}_{in}} \times 100$$

-continued
$$\text{O}_2 \text{ conversion (\%)} = \frac{\text{mol O}_{2_{in}} - \text{mol O}_{2_{out}}}{\text{mol O}_{2_{in}}} \times 100$$

Figure 3:
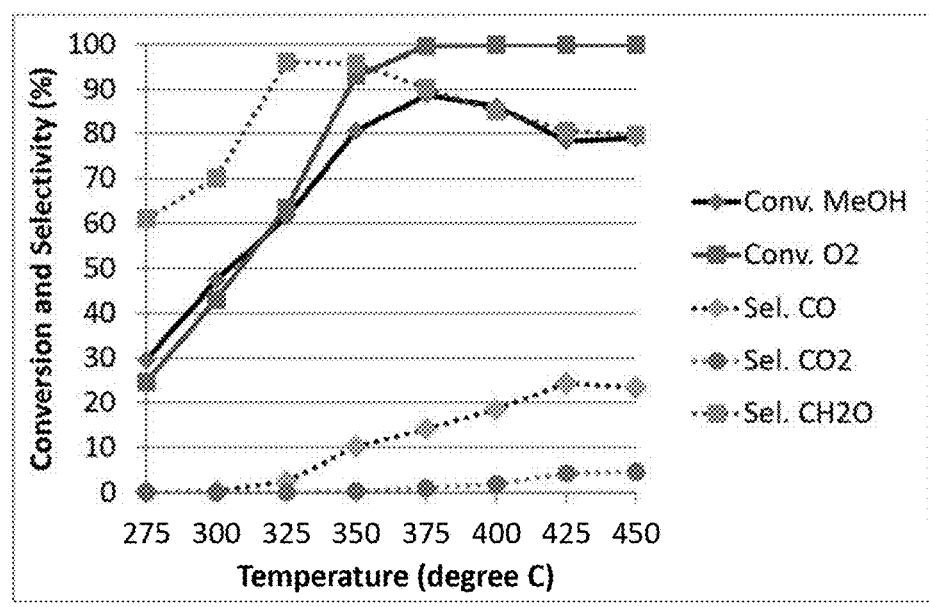
FIG. 3 shows reactant conversions and product selectivities obtained using a vanadium oxide catalyst having 1 wt % vanadium, with a gas stream having an $O_2/CH_3OH$ molar ratio of 0.5:1 over a temperature range of 275-450° C.
Figure 4:
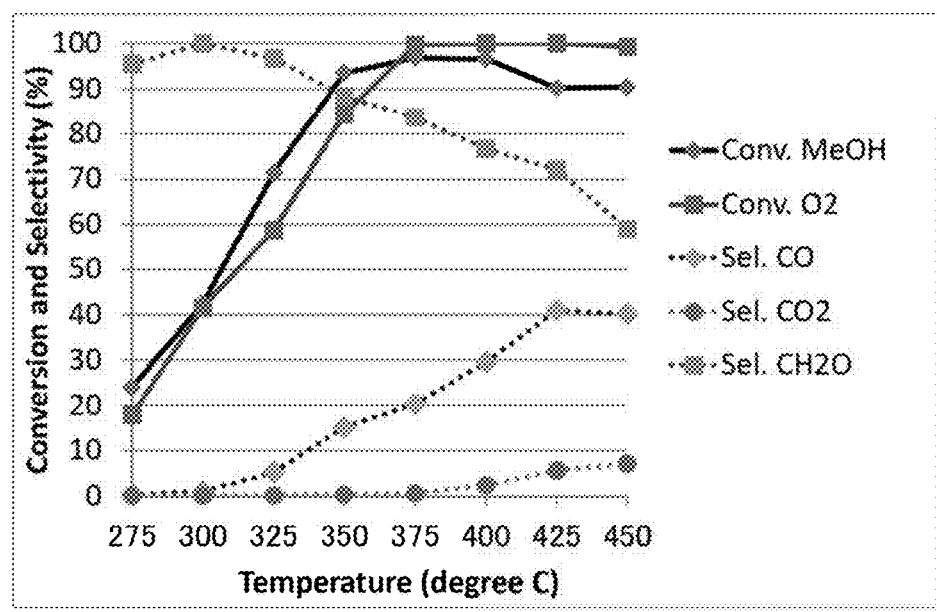
FIG. 4 shows reactant conversions and product selectivities obtained using a vanadium oxide catalyst having 1 wt % vanadium, with a gas stream having an $O_2/CH_3OH$ molar ratio of 0.6:1 over a temperature range of 275-450° C.
Figure 5:
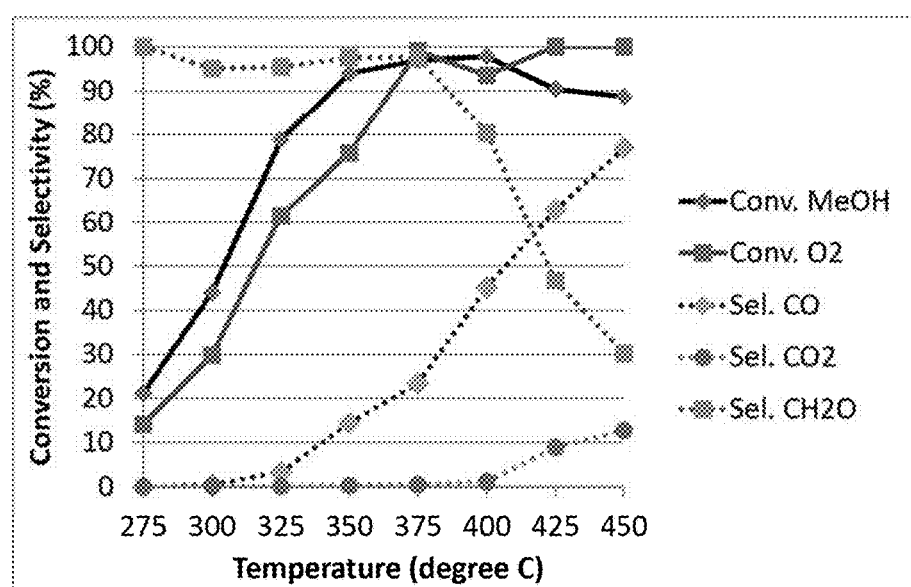
FIG. 5 shows reactant conversions and product selectivities obtained using a vanadium oxide catalyst having 1 wt % vanadium, with a gas stream having an $O_2/CH_3OH$ molar ratio of 0.7:1 over a temperature range of 275-450° C.
Figure 6:
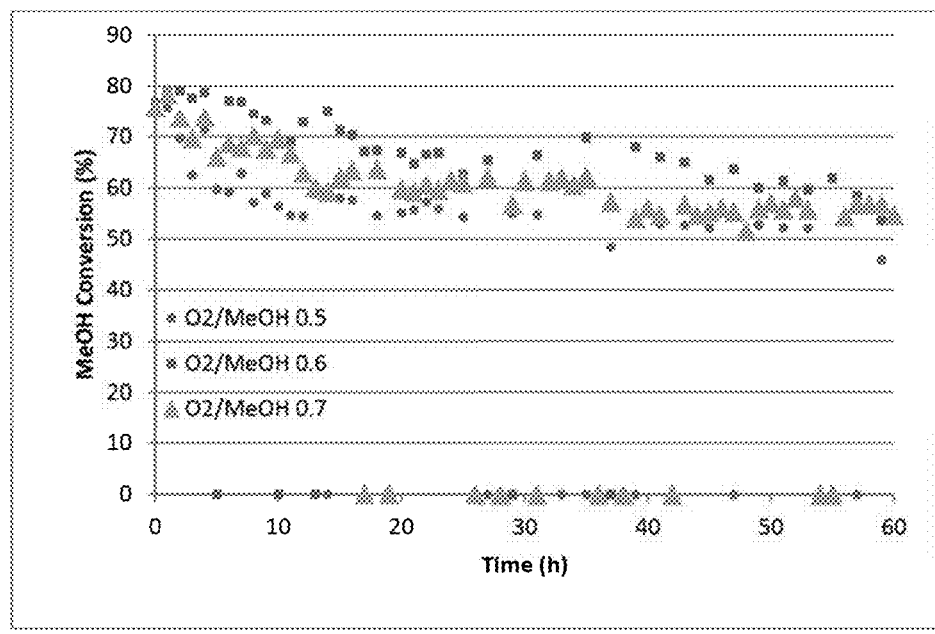
FIG. 6 shows the methanol conversion percentages obtained over 0-60 h using a vanadium oxide catalyst having 1 wt % vanadium, with an $O_2/CH_3OH$ molar ratio of 0.5:1, 0.6:1, or 0.7:1 and at a temperature of 325° C.

FIGS. 3, 4, and 5 show example conversion percentages of methanol and O$_2$ using a vanadium decorated catalyst with 0.7-1.3 wt %, preferably 0.8-1.2 wt % vanadium at temperatures of 275-450° C. and at O$_2$ to methanol molar ratios of 0.46:1-0.54:1, 0.56:1-0.64:1, and 0.66:1-0.74:1, respectively. For all three molar ratios, the conversion percentages of methanol and O$_2$ are generally higher at higher temperatures. FIG. 6 shows the conversion percentage of methanol for each of the three molar ratios over a 55-65 hour reaction period. Here, the O$_2$ to methanol molar ratio of 0.56:1-0.64:1 produces the highest methanol conversion percentage.

In one embodiment, at least 50 mol % of the methanol is converted to formaldehyde and at least one side product selected from the group consisting of hydrogen gas, carbon monoxide, carbon dioxide, water, and dimethyl ether. In other words, the percentage conversion of methanol is at least 50%. In one embodiment, a percentage conversion of methanol of at least 50% may occur at reaction conditions of 325-450° C. with an O$_2$ to methanol molar ratio of 0.48:1-0.74:1, and with a catalyst having a vanadium content of 0.7-1.3 wt %, preferably 0.8-1.2 wt % as shown in FIGS. 3-6. The at least 50% methanol conversion may also occur with the vanadium oxide catalyst with 2.7-3.3 wt %, preferably 2.8-3.2 wt % vanadium at reaction temperatures of 315-335° C., preferably 320-330° C. and with an O$_2$ to methanol molar ratio of 0.56:1-0.64:1, preferably 0.57:1-0.63:1 as shown in Table 2. In some embodiments, preferably the conversion of methanol is greater than 60% or greater than 70%.

The selectivity of a gas phase product is a stoichiometric mol % of the product produced per mole of a reactant converted or consumed. Here, the selectivities are based on the moles of methanol converted or consumed, which is CH$_3$O$_{in}$— CH$_3$OH$_{out}$, as expressed within the previous equations. A product having a selectivity of exactly 100% means that all of the reactant that was consumed went into a stoichiometric equivalent of that particular product. For example, in the catalytic process of the current invention, a formaldehyde selectivity of 100% means that every mole of methanol converted leads to a mole of formaldehyde produced. A product having a selectivity of exactly 0% means than none of the product was produced, regardless of whether or not reactant was converted. The percentage conversions for key products are:

$$\text{CH}_2\text{O selectivity (\%)} = \frac{\text{mol CH}_2\text{O}}{\text{mol of CH}_3\text{OH}_{consumed}} \times 100$$

$$\text{CO selectivity (\%)} = \frac{\text{mol CO}}{\text{mol of CH}_3\text{OH}_{consumed}} \times 100$$

$$\text{CO}_2 \text{ selectivity (\%)} = \frac{\text{mol CO}_2}{\text{mol of CH}_3\text{OH}_{consumed}} \times 100$$

Figure 7:
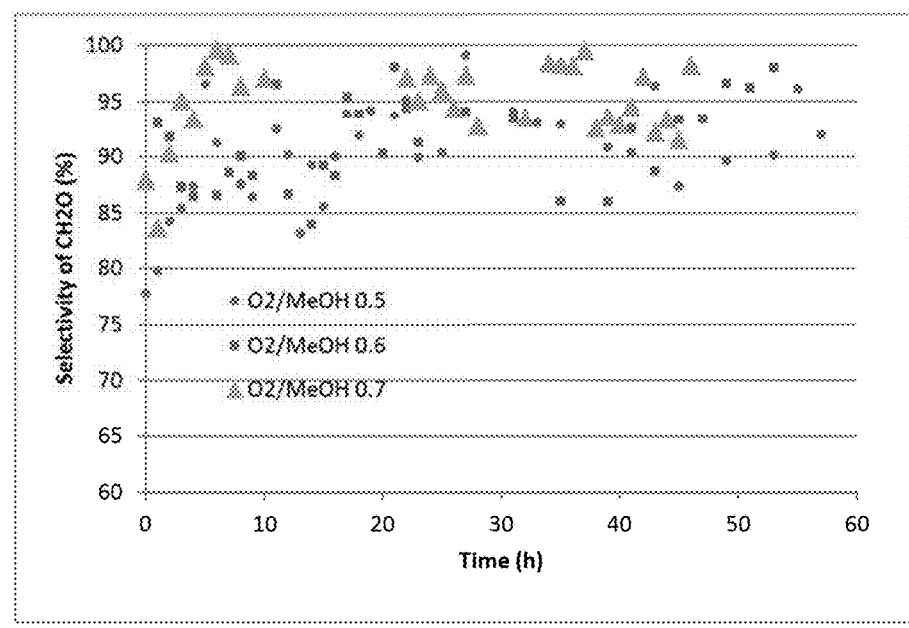
FIG. 7 shows the formaldehyde selectivities obtained over 0-60 h using a vanadium oxide catalyst having 1 wt % vanadium, with an $O_2/CH_3OH$ molar ratio of 0.5:1, 0.6:1, or 0.7:1 and at a temperature of 325° C.
Figure 8:
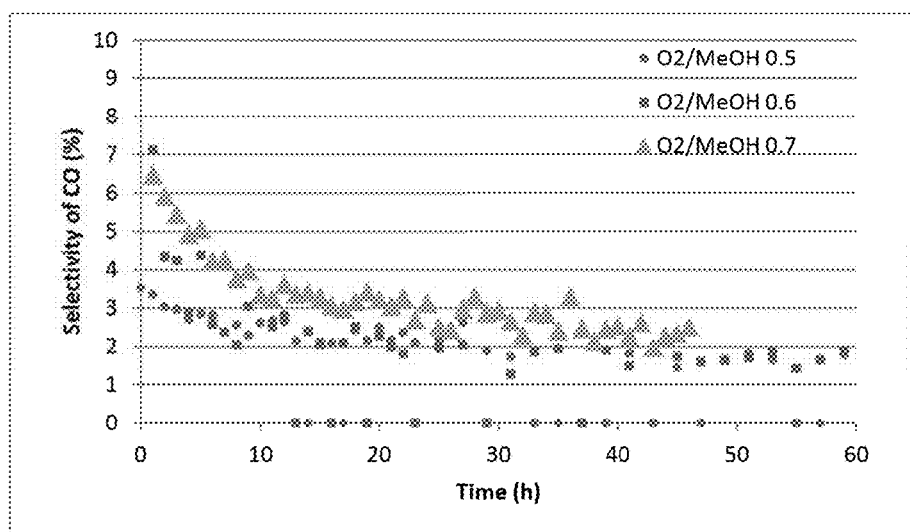
FIG. 8 shows the carbon monoxide selectivities obtained over 0-60 h using a vanadium oxide catalyst having 1 wt % vanadium, with an $O_2/CH_3OH$ molar ratio of 0.5:1, 0.6:1, or 0.7:1 and at a temperature of 325° C.
Figure 9:
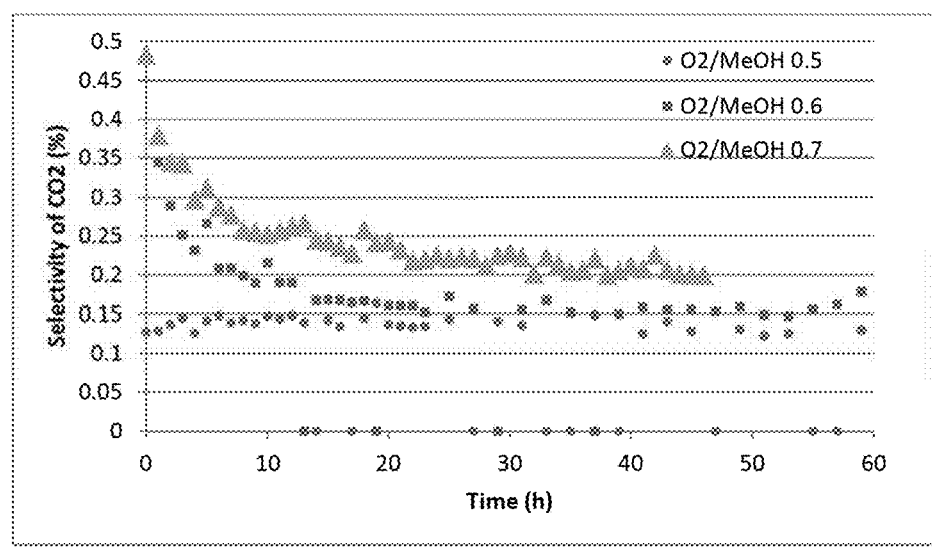
FIG. 9 shows the carbon dioxide selectivities obtained over 0-60 h using a vanadium oxide catalyst having 1 wt % vanadium, with an $O_2/CH_3OH$ molar ratio of 0.5:1, 0.6:1, or 0.7:1 and at a temperature of 325° C.

FIGS. 3-5 show example selectivities of CO, CO$_2$, and CH$_2$O (formaldehyde), using a vanadium decorated catalyst with 0.7-1.3 wt %, preferably 0.8-1.2 wt % vanadium at temperatures of 275-450° C. and at O$_2$ to methanol molar ratios of 0.5:1-0.7:1. The selectivities of formaldehyde tend to be greatest near the middle of the temperature range, while the selectivities of CO and CO$_2$ are greater at higher temperatures. FIG. 7 shows that for the 0.7-1.3 wt %, preferably 0.8-1.2 wt % vanadium catalyst at 315-335° C., preferably 320-330° C., the selectivities of formaldehyde at $O_2$ to methanol molar ratios of 0.46:1-0.74:1 increases slightly over the 0-30 h reaction time period. FIGS. 8 and 9 show that for the 0.7-1.3 wt %, preferably 0.8-1.2 wt % vanadium catalyst at 315-335° C. preferably 320-330° C., the selectivities of both CO and $CO_2$ tend to decrease over a reaction period of 0-45 h, or 0-60 h, with $O_2$ to methanol molar ratios of 0.46:1-0.54:1 and 0.56:1-0.64:1, showing the lowest selectivities.

In one embodiment, a selectivity percentage for formaldehyde from the partial oxidation of methanol is at least 90% (percentage based on moles). In other words, a mole percentage of formaldehyde produced with respect to moles methanol consumed is at least 90%. In a further embodiment, this selectivity percentage may occur when the gas stream has an $O_2$ to methanol molar ratio of 0.55:1.0-0.65:1.0, preferably 0.58:1.0-0.62:1.0, or about 0.6:1.0. In one embodiment, this may occur at reaction conditions of 325-375° C. with an $O_2$ to methanol molar ratio of 0.46:1-0.54:1, preferably 0.47:1-0.53:1 and a 0.7-1.3 wt %, preferably 0.8-1.2 wt % vanadium catalyst, as shown in FIG. 3. In one embodiment, this may occur at reaction conditions of 275-325° C. with an $O_2$ to methanol molar ratio of 0.56:1-0.64:1, preferably 0.57:1-0.63:1 and a 0.7-1.3 wt %, preferably 0.8-1.2 wt % vanadium catalyst, as shown in FIG. 4. In one embodiment, this may occur at reaction conditions of 275-375° C. with an $O_2$ to methanol molar ratio of 0.66:1-0.74:1, preferably 0.67:1-0.73:1, and a 0.7-1.3 wt %, preferably 0.8-1.2 wt % vanadium catalyst, as shown in FIG. 5. In another embodiment, catalysts with 2.2-3.8 wt % or 4.2-5.8 wt % vanadium may also produce formaldehyde selectivities greater than 90% when used at 320-330° C. with an $O_2$ to methanol molar ratio of 0.56:1-0.64:1, preferably 0.57:1-0.63:1, as shown in Table 2. In some embodiments, the selectivity percentage of formaldehyde may be at least 92% or at least 95%.

In one embodiment, a selectivity percentage for carbon dioxide from a conversion of methanol is 3% or less. In other words, a mole percentage of carbon dioxide produced with respect to moles methanol consumed is 3% or less. This may occur at reaction conditions of 275-400° C. with a 0.7-1.3 wt %, preferably 0.8-1.2 wt % vanadium catalyst and with an $O_2$ to methanol molar ratio of 0.46:1-0.54:1, 0.56:1-0.64:1, or 0.66:1-0.74:1, as shown in FIGS. 3, 4, and 5, respectively. FIG. 9 shows that with a 0.7-1.3 wt %, preferably 0.8-1.2 wt % vanadium catalyst at 315-335° C., preferably 320-330° C., the reactions at all three $O_2$ to methanol molar ratios are able to maintain carbon dioxide selectivities of 3% or less over 5-45 h, or 5-60 h, reaction periods. In another embodiment, catalysts with 2.7-3.3 wt %, preferably 2.8-3.2 wt %, or 5.7-6.3 wt %, preferably 5.8-6.2 wt %, vanadium may also produce carbon dioxide selectivities of 3% or less. In some embodiments, the selectivity of carbon dioxide may be 2% or less, or 1% or less.

In another embodiment, in the previously described reaction conditions where the percentage conversion of methanol is at least 50%, a selectivity percentage of carbon dioxide is 15% or less, preferably 12% or less, more preferably 10% or less.

In one embodiment, a selectivity percentage for carbon monoxide from a conversion of methanol is 10% or less. In other words, a mole percentage of carbon monoxide produced with respect to moles methanol consumed is 10% or less. This may occur at reaction conditions of 275-350° C. with an $O_2$ to methanol molar ratio of 0.46:1-0.54:1 and a 0.7-1.3 wt %, preferably 0.8-1.2 wt % vanadium catalyst, as shown in FIG. 3. In one embodiment, this may occur at reaction conditions of 275-325° C. with a 0.7-1.3 wt %, preferably 0.8-1.2 wt % vanadium catalyst being used with $O_2$ to methanol molar ratios of 0.56:1-0.64:1 and 0.66:1-0.74:1, as shown in FIGS. 4 and 5, respectively. FIG. 8 shows that with a 0.7-1.3 wt %, preferably 0.8-1.2 wt % vanadium catalyst at 315-335° C., preferably 320-330° C., reactions at all three $O_2$ to methanol molar ratios are able to maintain carbon monoxide selectivities of 10% or less over 0-45 h, or 0-60 h, reaction periods. In another embodiment, catalysts with 2.7-3.3 wt %, preferably 2.8-3.2 wt %, or 5.7-6.3 wt %, preferably 5.8-6.2 wt %, vanadium may also produce carbon monoxide selectivities of 10% or less. In some embodiments, the selectivity of carbon monoxide may be 6% or less, or 4% or less.

The catalyst reaction may enable the methanol partial oxidation reaction to continue at a stable reaction rate for several hours. For a fixed flow rate of the gas stream, a fixed temperature, and a fixed $O_2$ to methanol molar ratio, the stability of the reaction rate may be judged by monitoring a reactant conversion or a product selectivity over a period of time. In one embodiment, a conversion percentage for methanol is maintained at a value of at least 50%, preferably at least 55%, more preferably at least 56% for a reaction period of at least 50 hours, preferably at least 60 hours, more preferably at least 70 hours. In a further embodiment, over this reaction period, the selectivity of formaldehyde may be maintained at a value of at least 85%, preferably at least 90%. In one embodiment, this stable reaction rate may occur using an $O_2$ to methanol molar ratio of 0.56:1-0.64:1 with a 0.7-1.3 wt %, preferably 0.8-1.2 wt % vanadium catalyst at 315-335° C., preferably 320-330° C., for example, as shown in FIG. 7.

In one embodiment, the method further involves regeneration of the catalyst for use in another reaction experiment. The regeneration involves flowing a mixture of $O_2$ in helium over the vanadium oxide catalyst at a temperature of 450-550° C., preferably 475-525° C., more preferably 480-520° C. for 0.5-4 h, preferably 1-3 h. The mixture of $O_2$ in helium comprises 3-6 mol % $O_2$, preferably 3.5-4.5 mol % $O_2$ relative to the total moles of $O_2$ and He. The gas flow rate may be 30-70 cm$^3$/min, preferably 35-65 cm$^3$/min, more preferably 45-55 cm$^3$/min. This gas flowing and heating forms a regenerated catalyst which may then be reused for the partial oxidization of methanol into formaldehyde using reaction conditions as previously described, while maintaining a methanol conversion percentage of at least 50%. It is envisioned that the heating and the $O_2$ causes compounds adsorbed to the catalyst surface to react with $O_2$ and/or desorb. In another embodiment, the regenerated catalyst may be regenerated and reused at least 5 times, or at least 10 times. In other embodiments, the regeneration may use a gas stream with a much lower mol % $O_2$ for instance, 0.5-1 mol % $O_2$ in He, or may use pure He. Alternatively, the regeneration may use a higher mol % $O_2$ in He, such as 8-10 mol %, or 10-20 mol %. In other embodiments, nitrogen, argon, or some other inert gas may be used in place of the helium. The gas flow and temperature may be applied for the abovementioned length of time, or may be applied until products, such as CO, $CO_2$, or dimethyl ether, are no longer detected. In an alternative embodiment, the regeneration may be done using a substantially slower flow rate, such as 5-10 cm$^3$/min. In one embodiment, after regenerating a catalyst by flowing a mixture of 3-6 mol % $O_2$, the mol %

$O_2$ may be increased to 15-100 mol % or 20-100 mol % to ensure that no $CO_2$ or other reaction products are still being generated.

Figure 10:
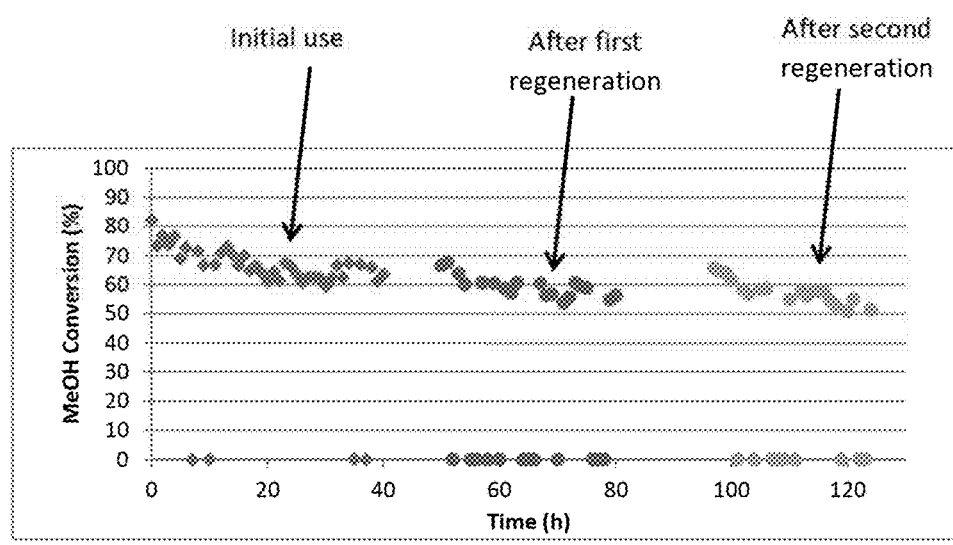
FIG. 10 shows the methanol conversion percentages obtained over time for a vanadium oxide catalyst being reacted with methanol a first time (initial use), being reacted with methanol after a first regeneration, and being reacted with methanol after a second regeneration.

FIG. 10 shows a methanol conversion percentage over time for a 0.7-1.3 wt %, preferably 0.8-1.2 wt % vanadium catalyst being used and regenerated twice. The catalyst was first reacted (initial use) at 315-335° C., preferably 320-330° C. with a gas stream having an $O_2$ to methanol molar ratio of 0.56:1-0.64:1. The catalyst was reacted for 0-40 h and then heated at 450-525° C. under a gas stream of 3.5-4.5 mol % $O_2$ in helium at a total flow rate of 45-55 cm$^3$/min, until $CO_2$ was no longer detected as a product. This produced a regenerated catalyst. To check that $CO_2$ was no longer being generated, the regenerated catalyst was exposed to 18-22 mol % $O_2$ in He for 0.75-1.25 hour, and then with pure $O_2$ for 2.5-3.5 h, both at 450-525° C. and total flow rates of 45-55 cm$^3$/min. The catalyst was then reacted using the initial conditions, then regenerated a second time and reacted again. Over these three reactions, the catalyst was able to maintain a methanol conversion of at least 50%, preferably at least 55%.

The examples below are intended to further illustrate protocols for preparing, characterizing, and using the vanadium oxide catalyst, and are not intended to limit the scope of the claims.

Example 1

Preparation of a Mixed Oxide Support of $CeO_2$ and $ZrO_2$ 30 g of $CeO_2$ (ACROSS, 99.9%) and 10 g of $ZrO_2$ (Aldrich, 99%) were added to 50 cm$^3$ of deionized water in a glass beaker to prepare a suspension. The suspension was then sonicated for 60 min in order to mechanically homogenize the mixture of $CeO_2$ and $ZrO_2$. After the sonication, the suspension was dried in an oven at 120° C. overnight. After the drying, the mixed support of $CeO_2$ and $ZrO_2$ was obtained, with a $CeO_2$:$ZrO_2$ weight ratio of 3:1. BET surface area of the prepared support was determined to be 7.4 m$^2$/g.

Example 2

Preparation of V/$CeO_2$—$ZrO_2$ Catalyst

Vanadium oxide was supported on a $CeO_2$—$ZrO_2$ mixed oxide by an incipient wetness impregnation process. To prepare 5 g of 1 wt % V supported on $CeO_2$—$ZrO_2$ catalyst, 0.1171 g of $NH_4VO_3$ (Aldrich, 99%) was dissolved in 10 mL of deionized water at 65° C., resulting in a yellow solution. 5 g of $CeO_2$—$ZrO_2$ mixed oxide support, which was prepared in Example 1, was then added to the $NH_4VO_3$ aqueous solution. Water was then evaporated by using a rotary evaporator set at 40° C. with a vacuum pressure of 40-60 mbar. After completing the evaporation, an orange-yellowish powder was collected and dried in an oven at 110° C. for 3 h. The powder was then calcined in the static air at 500° C. for 5 h. The needed temperature was attained by increasing the oven temperature from 25° C. to 500° C. by a ramping rate of 5° C. min$^{-1}$.

Figure 1:
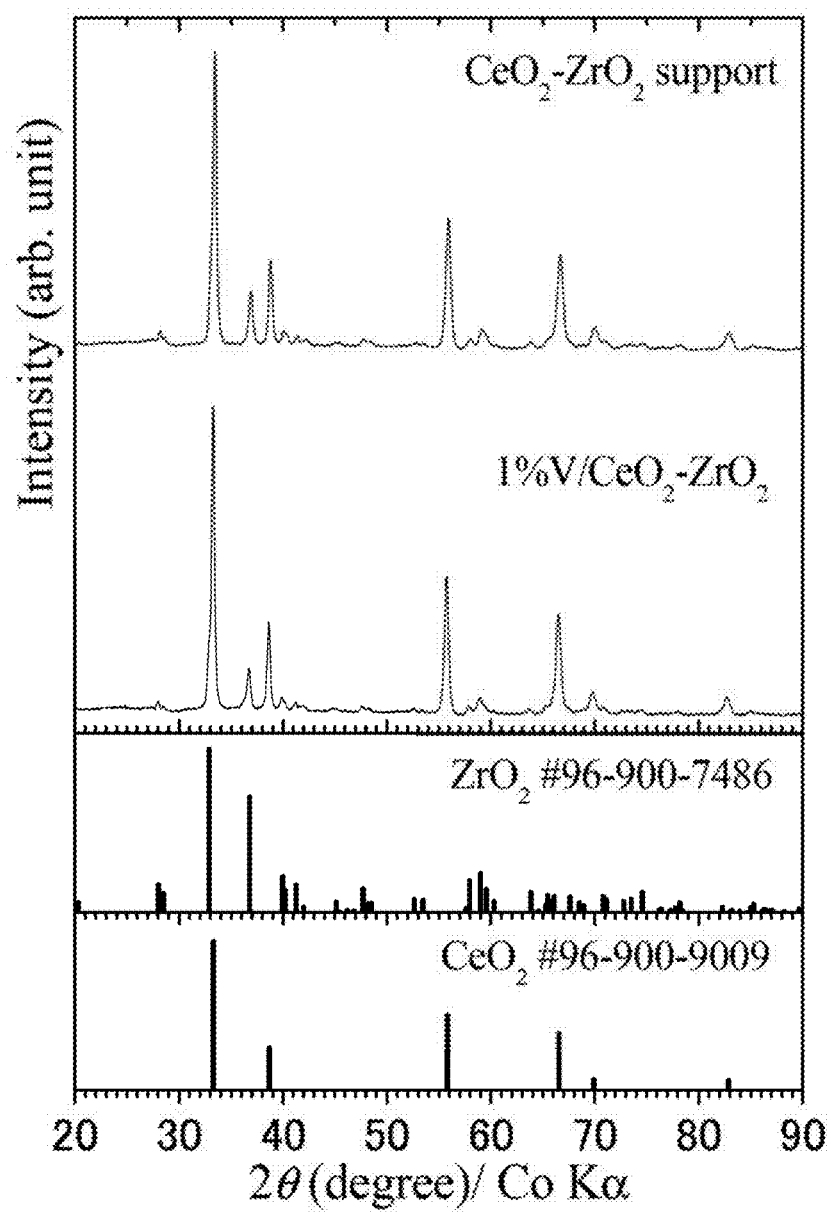
FIG. 1 shows X-ray diffraction (XRD) patterns of a $CeO_2$ and $ZrO_2$ composite core without vanadium oxide, a $CeO_2$ and $ZrO_2$ composite core with vanadium oxide nanoparticles, and reference XRD patterns of individual $ZrO_2$ and $CeO_2$.

The obtained powder material was tableted, and the tablets were ground. A fraction with a grain size between 0.01 and 0.08 mm was selected and used for catalytic activity and selectivity measurements. The BET surface area of 1% V/$CeO_2$—$ZrO_2$ catalyst was 7.9 m$^2$/g. On the XRD pattern of the 1% V/$CeO_2$—$ZrO_2$ sample, only peaks from $CeO_2$ and $ZrO_2$ were detected. Probably V concentration is very low (FIG. 1), suggesting that crystallinity of vanadium oxide was low or V particles are smaller than the detection limit of the instrument. Additionally, TEM observation revealed that nanoparticles of $V_2O_5$ with 2-5 nm diameter were formed on the surface of the support particles (FIG. 2).

Example 3

Partial Oxidation of Methanol Over V/$CeO_2$—$ZrO_2$ to Formaldehyde at a Stoichiometric Ratio of $O_2$:MeOH=0.5 in the Reaction Mixture at the Reactor Entrance The process of partial oxidation of methanol (POM) was carried out using a fixed bed quartz microreactor (PID Eng & Tech, System, Spain) at atmospheric pressure and between 275 and 450° C. The reactor was charged with 0.1 g of catalyst with grain sizes of 0.01 to 0.08 mm. The catalyst bed was supported on a bed of quartz wool. The inner diameter of the quartz reactor was 4 mm, and the height of the catalyst was 7-8 mm. A K-type thermocouple was placed at the center of the catalyst bed.

Liquid methanol flow was controlled by a Bronkhorst High-Teck B.V. CEM system at a 0.45 g h$^{-1}$ flow rate. Oxygen flow was maintained at an $O_2$/MeOH molar ratio of 0.5:1 by a mass flow controller (Bronkhorst High-Teck B.V.).

The required methanol and oxygen flow were mixed with helium in a mixing chamber which was heated at 150° C. The total flow of oxygen, methanol, and inert He was 50 cm 1 min, and the gas hourly space velocity (GHSV), or gas hourly flow rate per mass of catalyst, was 30,000 cm$^3 \cdot$h$^{-1} \cdot$g$_{cat}^{-1}$.

The catalyst bed was preheated to 250° C. prior to introducing the reactants to the reactor. The reactor temperature was then increased to 275° C. at a ramping rate of 5° C./min. For each desired experimental condition, a temperature between 275 and 450° C. was held for 3 h to reach steady-state prior to analyzing the reaction products. The reactants and products were analyzed with an on-line gas chromatograph (HP, G1540A) equipped with TCD detectors. A molecular sieve 13X was used to separate $O_2$ and CO, and a Porapak QS was used to separate $H_2$, $CH_4$, $CO_2$, $H_2O$, $CH_2O$ and $CH_3OH$.

The conversions (%) of the reactants and the selectivity of products were calculated as follows:

$$CH_3OH \text{ conversion}(\%) = \frac{\text{mol. of } CH_3OH_{in} - \text{mol. of } CH_3OH_{out}}{\text{mol. of } CH_3OH_{in}} \times 100$$

$$O_2 \text{ conversion } (\%) = \frac{\text{mol. of } O_{2_{in}} - \text{mol. of } O_{2_{out}}}{\text{mol. of } O_{2_{in}}} \times 100$$

$$CH_2O \text{ selectivity } (\%) = \frac{\text{mol. of } CH_2O}{\text{mol. of } CH_3OH_{consumed}} \times 100$$

$$CO \text{ selectivity } (\%) = \frac{\text{mol. of } CO}{\text{mol. of } CH_3OH_{consumbed}} \times 100$$

$$CO_2 \text{ selectivity } (\%) = \frac{\text{mol. of } CO_2}{\text{mol. of } CH_3OH_{consumed}} \times 100$$

Example 4

Partial Oxidation of Methanol Over V/$CeO_2$—$ZrO_2$ to Formaldehyde at Different $O_2$/MeOH Ratios.

The partial oxidation of methanol (POM) was carried out by the same method and the same experimental setup as described in Example 3 but with changes in the $O_2$/MeOH ratio. $O_2$ flow rate was adjusted to fix the $O_2$/MeOH molar ratio at 0.6:1 and 0.7:1. Fresh 1% V/$CeO_2$—$ZrO_2$ catalyst was set in the reactor for each POM reaction.

Even at these $O_2$/MeOH ratios, which are higher than the stoichiometric condition of $O_2$/MeOH=0.5:1, the 1% V/$CeO_2$—$ZrO_2$ catalyst showed a formaldehyde selectivity which was higher than 90% at 325° C. (FIG. 3). FIGS. 3, 4, and 5 show the conversion and selectivity rates for the 1% V/$CeO_2$—$ZrO_2$ catalyst over 275-450° C. at $O_2$/MeOH molar ratios of 0.5:1 (stoichiometric condition), 0.6:1, and 0.7:1, respectively.

Example 5

Partial Oxidation of Methanol to Formaldehyde Over V/$CeO_2$—$ZrO_2$ with Different V Content.

V/$CeO_2$—$ZrO_2$ catalysts with vanadium content of 3 and 5 mass % were prepared by the incipient wetness impregnation method as described in Example 2. The partial oxidation of methanol on 3% V/$CeO_2$—$ZrO_2$ and 5% V/$CeO_2$—$ZrO_2$ was carried out by the same method using the same experimental setup as described in Example 3 but with the $O_2$/MeOH molar ratio fixed at 0.6.

The methanol conversion and selectivity to formaldehyde at 325° C. are organized in Table 2. As a result, all catalysts showed high $CH_2O$ selectivity (>95%). Methanol conversion decreased with increasing V content. The 1% V/$CeO_2$—$ZrO_2$ catalyst showed the highest activity.

TABLE 2

Methanol conversion and selectivity to formaldehyde brought by V/$CeO_2$-$ZrO_2$ catalysts with different V content

| Catalyst | Methanol conversion (%) | $CH_2O$ selectivity (%) |
|---|---|---|
| 1% V/$CeO_2$-$ZrO_2$ | 71 | 97 |
| 3% V/$CeO_2$-$ZrO_2$ | 51 | 100 |
| 5% V/$CeO_2$-$ZrO_2$ | 45 | 99 |

Example 6

Durability Test of V/$CeO_2$—$ZrO_2$ on the Partial Oxidation of Methanol with Different $O_2$/MeOH Ratios.

The partial oxidation of methanol was carried out by the same experimental setup and conditions as those described in Example 3, but keeping the reaction temperature constant at 325° C. for a long run of 60 h with one of three $O_2$/MeOH ratios. Reactant flow having a $O_2$/MeOH molar ratio of 0.5:1, 0.6:1, or 0.7:1 was supplied to a fresh 1% V/$CeO_2$—$ZrO_2$ catalyst which had been pre-heated at 250° C. Then, the temperature of the catalyst was ramped up to 325° C. at 5° C./min. Conversion and selectivity data were evaluated with time at an isothermal condition of 325° C.

All catalysts showed a decrease of MeOH conversion during the initial 10 h of operation. At an $O_2$/MeOH molar ratio of 0.6:1, the catalyst showed the highest MeOH conversion. For all three $O_2$/MeOH molar ratios, the catalyst showed high formaldehyde selectivity, which was above 90%. The selectivity of CO and $CO_2$ were less than 5% for all cases. In addition, CO and $CO_2$ selectivities at an $O_2$/MeOH molar ratio of 0.6:1 were almost equal to those at an $O_2$/MeOH molar ratio of 0.5:1 after 10 h from the start of the reaction. These results suggest that a little excess of $O_2$ above the stoichiometric condition improves the activity and stability of the catalyst without affecting CO and $CO_2$ selectivity. FIG. 6 shows the MeOH conversion over the 60 h reaction for each of the three $O_2$/MeOH molar ratios while FIGS. 7, 8, and 9 show the selectivities of formaldehyde, CO, and $CO_2$, respectively.

Example 7

Regeneration of the V/$CeO_2$—$ZrO_2$ Catalyst

After partial oxidation of methanol at 325° C. and an $O_2$/MeOH molar ratio of 0.6:1, regeneration of the 1% V/$CeO_2$—$ZrO_2$ catalyst was carried out under 02 flow. The catalyst was heated from 250° C. to 500° C. at a ramping rate of 1° C./min under 4% $O_2$ (in He) at a total flow rate of 50 $cm^3$/min. The temperature was held at 500° C. with 4% $O_2$ flow until $CO_2$ generation was finished. Then, the catalyst was regenerated at 500° C. with total flow rates of 50 $cm^3$/min 20% $O_2$ in He for 1 h, and pure Or for 3 h. When the catalyst was exposed to flows of 20% $O_2$ in He and then pure $O_2$, GC analysis confirmed that no $CO_2$ was generated.

After the regeneration, the catalyst was cooled down to 250° C. and tested on the partial oxidation of methanol with the same conditions as the fresh catalyst.

After this second activity test, the catalyst was regenerated again with only 4% $O_2$ flow. The catalyst was heated from 250 CC to 500° C. at 1° C./min under 4% $O_2$ (in He) with a total flow rate of 50 $cm^3$/min. The temperature was held at 500° C. with the 4% $O_2$ flow until $CO_2$ generation finished. The catalyst was then cooled down to 250° C. and tested on the partial oxidation of methanol with same condition as the fresh catalyst.

As a result, it was shown that the heat treatment at 500° C. under a flow of 4% $O_2$ (in He) could regenerate the catalyst. FIG. 10 shows the MeOH conversion of a fresh catalyst, the conversion after the first regeneration, and the conversion after the second regeneration.

The invention claimed is:

1. A vanadium oxide catalyst, comprising
   a $CeO_2$ and $ZrO_2$ composite core decorated with vanadium oxide nanoparticles,
   wherein the vanadium oxide nanoparticles have diameters of 1-10 nm,
   wherein the vanadium oxide catalyst has a diameter of 5-80 μm and comprises from 0.1 to 3 wt % vanadium relative to a total weight of the vanadium oxide catalyst, and
   wherein the vanadium oxide nanoparticles are in a crystalline phase and cover 10-90% of the total surface area of the composite core.

2. The vanadium oxide catalyst of claim 1, which has a surface area of 5-10 $m^2·g^{-1}$.

3. The vanadium oxide catalyst of claim 1, which has a Ce to Zr mass ratio of 2.0:1.0 to 3.5:1.0.

4. The vanadium oxide catalyst of claim 1, wherein the vanadium oxide is $V_2O_5$.

5. A method for producing the vanadium oxide decorated catalyst of claim 1 comprising:
   sonicating $CeO_2$ powder and $ZrO_2$ powder in a liquid suspension to form a mixed oxide;
   mixing the mixed oxide with a vanadium precursor to form an aqueous suspension;
   drying the aqueous suspension to produce a dried catalyst precursor;
   heating the dried catalyst precursor at 450-700° C. for 2-8 hours to produce a calcined powder; and
   pelletizing and grinding the calcined powder to produce the vanadium oxide catalyst.

6. The method of claim 5, wherein the aqueous suspension has a vanadium concentration of 0.05 to 1.0 M.

7. The method of claim 5, wherein the vanadium precursor is one selected from the group consisting of ammonium metavanadate, potassium metavanadate, sodium metavanadate, bismuth vanadate, vanadium oxytrichloride, and vanadium pentafluoride.

8. The method of claim 7, wherein the vanadium precursor is ammonium metavanadate.

9. A method of partially oxidizing methanol into formaldehyde comprising:

feeding a gas stream comprising $O_2$ and methanol to a catalyst bed comprising the vanadium oxide catalyst of claim 1 at a temperature of 275-380° C. to produce formaldehyde and at least one side product selected from the group consisting of hydrogen gas, carbon monoxide, carbon dioxide, water, and dimethyl ether.

10. The method of claim 9, wherein the gas stream has an $O_2$ to methanol molar ratio of 0.5:1.0 to 0.8:1.0.

11. The method of claim 9, wherein the gas stream is fed to the catalyst bed at a gas hourly flow rate per g of the vanadium oxide catalyst of 25,000 to 35,000 $cm^3 \cdot h^{-1} \cdot g^{-1}$.

12. The method of claim 9, wherein a mole percentage of formaldehyde produced with respect to moles methanol consumed is at least 90%.

13. The method of claim 12, wherein the gas stream has an $O_2$ to methanol molar ratio of 0.55:1.0 to 0.65:1.0.

14. The vanadium oxide catalyst of claim 1, wherein the vanadium oxide nanoparticles cover 20-80% of the total surface area of the composite core.

15. The vanadium oxide catalyst of claim 14, wherein the vanadium oxide nanoparticles cover 20-50% of the total surface area of the composite core.

16. The vanadium oxide catalyst of claim 1, wherein the vanadium oxide nanoparticles have diameters of 1-8 nm.

17. The vanadium oxide catalyst of claim 16, wherein the vanadium oxide nanoparticles have diameters of 2-5 nm.

18. The vanadium oxide catalyst of claim 1, which has a diameter of 10-75 μm.

19. The vanadium oxide catalyst of claim 18, which has a diameter of 30-70 μm.

* * * * *